United States Patent [19]

Arnhem

[11] 4,244,466
[45] Jan. 13, 1981

[54] CONTACT LENS APPLICATOR

[76] Inventor: Erik M. Arnhem, P.O. Box 46053, Hollywood, Calif. 90046

[21] Appl. No.: 82,811

[22] Filed: Oct. 9, 1979

[51] Int. Cl.³ .................. B65D 85/00; B08B 3/10; A61F 9/00; A45C 11/04
[52] U.S. Cl. .................................. 206/5.1; 294/1 CA
[58] Field of Search ............... 206/5.1; 294/1 CA, 64

[56] References Cited

U.S. PATENT DOCUMENTS

| 3,063,083 | 11/1962 | Obitts | 206/5.1 |
|---|---|---|---|
| 3,129,971 | 4/1964 | Kobler | 294/1 CA |
| 3,150,406 | 9/1964 | Obitts | 206/5.1 |
| 3,251,459 | 5/1966 | Lacour | 206/537 |
| 4,088,359 | 5/1978 | Buchanan, Jr. | 294/1 CA |

FOREIGN PATENT DOCUMENTS 1197161  7/1970  United Kingdom .................. 206/5.1

*Primary Examiner*—William T. Dixson, Jr.

[57] ABSTRACT

Contact lens applicator, comprising a container with closure, an apertured contact lens accommodating tray extending perpendicularly from the closure for vertical placement within the container, a member slidable over the tray and provided with apertures which may be brought in alignment with those of the tray.

10 Claims, 4 Drawing Figures

U.S. Patent
Jan. 13, 1981
4,244,466
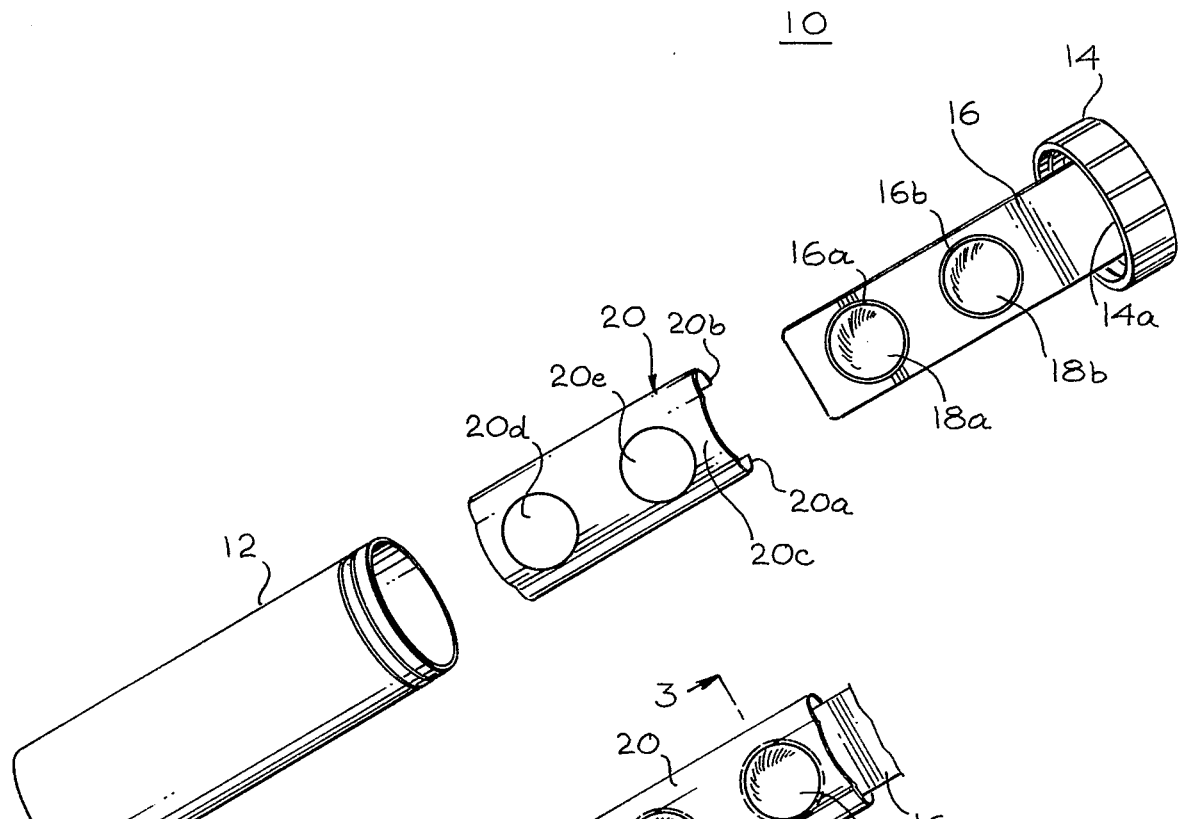
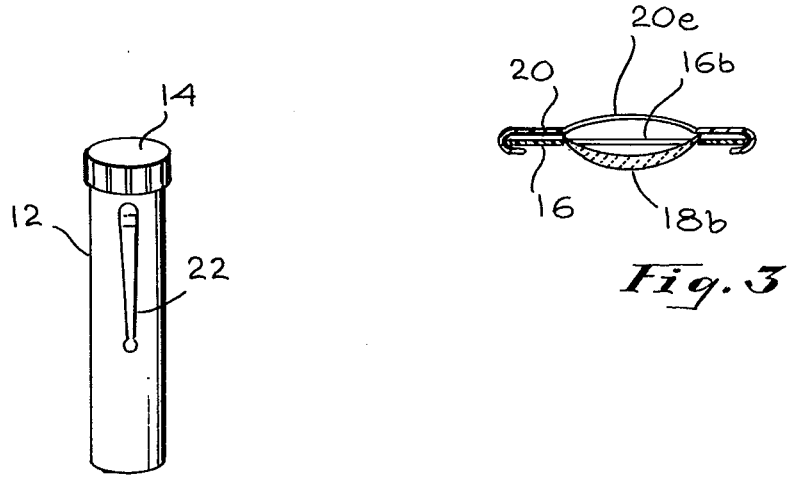

CONTACT LENS APPLICATOR

FIELD OF THE INVENTION

Several drawbacks exist with respect to cleaning and applying a contact lens onto the eyeball, especially when the contact lens wearer has no immediate access to tap water.

Firstly, it is extremely important that the hands be washed thoroughly prior to touching the contact lens so as not to cause an infection to the eye.

Secondly, when, generally applying the contact lens, the latter is placed on a fingertip and the clarity of the outer lens surface will be adversely affected by the moisture or secretions of the finger.

Thirdly, when a contact lens has been applied and float on the cornea of the eye, the wearer of the lens frequently experiences a pain or discomfort in the eye, normally caused by a tiny foreign object, e.g., a hair trapped between the inner surface of the lens and the cornea, or by a film of mucus forming on the lens; if this occurs when the contact lens wearer is driving a car, or works at a location where water is not readily available, the contact lens wearer must remove, and somehow try to clean and reinsert the lens with contaminated hands.

There is, therefore a need to conceive a device which will enable the contact lens wearer—when e.g., getting up in the morning, during work, driving, etc.—to rinse and reinsert a contact lens without direct use of the hands.

The applicator, according to the invention, is, furthermore less bulky than the conventional leak proof storage cleansing contact lens container and incorporates means for storing and actually cleaning the contact lens and applying the latter directly onto the eye from the invented applicator; moreover, the danger of losing a contact lens while cleaning or handling same is practically eliminated by avoiding direct manipulation of a wetted contact lens.

It should also be noted, that the conventional contact lens storage/cleansing container is not used for actively cleaning the lens but merely causes the latter to float in a chemical solution poured into the container.

SUMMARY OF THE INVENTION

In addition to what is stated above, the device, according to the invention, entails a new concept in the storage/cleansing of and applying a contact lens. Contrary to the present way of placing contact lenses in a storage/cleaning container, the invention provides for a narrow apertured tray, extending vertically from the top of and within a container; the contact lens is then positioned vertically in an appropriately dimensioned aperture in the tray, with the interior lens surface facing outwardly and lying substantially flush with the periphery of the aperture.

An apertured sliding member is provided, intended for back and forth sliding over the tray, causing its aperture(s) to coincide with that/those of the tray, and thus lock the lens in an aperture of the tray, or, alternately, to fully expose an aperture of the tray for removal of the lens from the tray.

By virtue of the coinciding apertures of the tray and sliding member, water or storage/cleaning fluid may reach all areas of the contact lens accommodated in the tray. The diameters of the apertures of the tray and sliding member are substantially identical or may be decreasing somewhat in depth relative to or perhaps slightly smaller than the diameter of the contact lens, and the latter thus cannot escape through either of the overlapping apertures, but is locked there within.

Furthermore, an elongated center portion of the sliding member may be raised or curved slightly, that is, at a lesser height than that of the contact lens, forming an open ended channel along the length of the sliding member, so that the fluid, additionally may flow through the thusly created channel into the interior surface of the contact lens. Since the height of the raised center portion of the sliding member is less than that of the contact lens, the latter may, when subjected to fluid pressure from below, rise slightly in its apertured seat in the tray, but cannot—regardless of the width of the channel of the sliding member—slip through same.

Thus, when the contact lens is in place in the aperture of the tray and the sliding member is properly superposed on the tray, the fluid in the container is capable of effectively reaching, for cleansing purposes, all areas of the contact lens, being subjected to a swishing action of the fluid.

Due to the vertical position of the contact lens (or lenses) in the container, the dimensions of the container may be extremely narrow, e.g., 8 mm (depth)×15 mm (width)×40 mm (length). The container for the contact lens(es) may, then, if provided with a holder or clip, be carried as a pen in a shirt pocket, bag, etc., without risking leakage of fluid therefrom.

Such a container may actually incorporate a real writing instrument, which, when in use, will carry out the swishing action of the fluid therein.

Thus, the device, according to the invention, carries out effective cleansing of a contact lens as well as serving as an applicator of the contact lens directly to the eye without manually touching same. The described features of the device are, as noted, of particular importance, when the contact lens wearer does not have access to water for cleaning of hands and lenses.

It is, therefore an object of the invention to provide a self-contained device for storing and cleaning of contact lenses and their direct transfer therefrom to the eyes, respectively.

It is a further object of the invention to provide such a device, dimensioned to be carried in the pocket as a pen or the like.

It is still a further object to provide such a device which will require a minimum of manual handling of the contact lenses accommodated therein.

BRIEF DESCRIPTION OF THE DRAWINGS

FIG. 1 is an exploded perspective view of the device, according to the invention, comprising a container, with a closure from which a tray extends, and a sliding member, slidable over the tray.

FIG. 2 is a fragmentary perspective view of the tray and sliding member superposed thereon.

FIG. 3 is a sectional view of tray and sliding member on line 3—3 of FIG. 2, with a contact lens seated in the tray.

FIG. 4 is a perspective exterior view of the device, according to the invention, provided with a pen clip.

PREFERRED EMBODIMENT OF THE INVENTION

In the drawings like reference numbers indicate identical parts in the various views thereof. In the drawings, numeral 10 indicates the device or applicator, according to the invention in its entirety. As illustrated in the drawings; housing means, e.g., a container 12 for the contact lenses (FIGS. 1 and 4) is of cylindric shape and closure 14 may be adapted to be screwed onto the container, or otherwise appropriately fastened thereto. Container 12 and closure 14 may, of course be of any suitable shape, such as oval, rectangular, etc., that is adaptable to placement in a pocket, bag, etc.

Means for accommodating and ocularly inserting the contact lens(es), e.g., a narrow thin tray 16 is mounted perpendicularly to (or extends integrally from) an off-centered interior portion of closure 14 and inserted in container 12 when closure 14 is mounted over the opening of the container. The primary reason for the trays' 16 off-centered position relative to closure 14 is to facilitate the direct transfer of the contact len(es) therefrom to the eye(s). Tray 16 is provided with two apertures 16a, 16b, spaced appropriately from one another. The diameter of apertures 16a or 16b is approximately 10 mm (or 5/16 of an inch) in the case a standard sized 10 mm (5/16") diameter lens 18 is intended for accommodation therein. The preferred length, width and depth of tray 16 are, respectively 40–60 mm, 15 mm and 8 mm. The interior surface of contact lens 18 is, when placed in aperture 16a or b of tray 16, facing upwardly in FIG. 3. Due to the relative dimensions of contact lens 18 and aperture 16a or b, the upper rim of the former will lie substantially flush with, or slightly above the periphery of aperture 16a or b, and cannot drop through aperture 16a,b.

The surface of tray 16, lying closest to the outer edge or rim of closure 14 is considered, for the purpose of describing the present invention, the top surface from which contact lens 18 is transferred to the eye, and subsequently returned to for cleansing and storage.

Retaining means for the contact lens(es), e,g., a sliding member 20, is provided with downward and inwardly directed edges forming longitudinal openended passages 20a, 20b, into which the edges of tray 16 slides, so that tray 16 will underlie sliding member 20; furthermore, sliding member 20 may have a slightly raised or curved open-ended center portion 20c, extending along the entire length of the upper surface of sliding member 20, the preferred length of which is about 30–40 mm.

Sliding member 20 is provided with two apertures 20 d,e, spaced apart from one another at the same distance as apertures 16a,b of tray 16, and are intended to coincide with the latter. The diameter of apertures 20d,e is substantially identical to or slightly smaller than that of contact lens 18, so that the latter, when positioned in apertures 16a,b and apertures 20d,e and 16a,b, respectively are caused to coincide with each other, cannot either escape through apertures 20d,e. As noted, the height of the raised portion 20c of sliding member 20 is less than that of contact lens 18 and therefore the latter can also not pass through the raised portion 20c (FIG. 1).

Thus, all surfaces of contact lens 18 are accessible to the cleansing fluid, to be poured into container 12, even the rim of contact lens 18, which—due to the clearance provided by the raised center portion 20c of sliding member 20—may off and on rise slightly in its seat (aperture 16a or b), when the fluid is vigorously swished in the container, causing the fluid to effectively come in contact with the contact lens rim. When the sliding member 20 is pushed backwardly relative to tray 16, the contact lens(es) will be fully exposed in apertures 16a,b, ready for direct application therefrom to the eye(s).

In FIG. 4, the applicator, according to the invention, is shaped as a pen or pencil with holding means, e.g., a clip 22, for convenient attachment to a pocket, or the like.

It should be noted, that sliding member 20, obviously could be formed as a flat apertured slide without a raised center portion, and function effectively, although the swishing action of the fluid, then may be somewhat diminished.

The mode of operation of the applicator is as follows:

(1) When the contact lenses are removed from the eyes, e.g., at bed time, or to relieve the eyes, one should first, if possible, wipe or rinse them clean.

Sliding member 20, superposed on tray 16, is then slit in the direction away from closure 14 of container 12, so as to expose the apertured portion of tray 16; the contact lenses 18 are placed in apertures 16a,b, respectively; slide 20 is pushed back so that its apertures 20d,e align with apertures 16a,b, thus interlocking contact lenses 18 there between, as explained above. Container 12 is filled with storage/cleaning fluid to about half its volume. When closure 14 is securely fastened to container 12, contact lenses 18, sandwiched between tray 16 and slide 20, will lie securely within container 12. When the fluid in container 12 is swished vigorously, the fluid will forcefully flow (as indicated by arrows, FIG. 2) through apertures 16a, b, 20d,e and raised slide portion 20c of the device, rinsing and wetting contact lenses 18.

Suggested Application of a Contact Lens.

(2) When the contact lenses are to be reinserted in the eyes (e.g., when getting up in the morning): Hold closure 14 in the left hand between index (or middle) finger and thumb; push back slide 20 so as to expose lens 18b in aperture 16b; pull down gently the lower left eye lid with the right index finger (and the upper lid upwardly with the left index finger, if free) to broaden the visual cornea surface; bring lens 18b in aperture 16b close to the left eye, by looking straight into aperture 16b, and transfer lens 18b to the eye; push slide 20 further back (or remove) to expose contact lens 18a in aperture 16a; now hold closure with right hand and pull the lower right eye lid with your left index finger, etc., repeat the same procedure in applying the right contact lens, as described above. Thus, the cleaning and applying steps for the contact lenses were carried out, according to the above instructions, without directly touching them with one's hands.

When removing the contact lenses from the eyes for placement of same in apertures 16a, b, it may be possible to again avoid the direct touch of the hands, by carefully bringing the eyes, respectively close to apertures 16a, b, so that the contact lenses will drop into the apertures.

As it appears from the above description, the device, according to the invention, may not only be used as a contact lens cleaning and applying device in "emergency" situations, (e.g., no access to tap water) but also under normal conditions, in which case the contact lens wearer, e.g., at bedtime may, on removing the contact lenses, clean same thoroughly and then place them in the applicator, for subsequent application, e.g., in the morning, without first again subjecting the lenses to manual rubbing, rinsing, etc.

It would also be possible to rinse, rub and clean the contact lenses while retained between tray 16 and elongated member 20, prior to direct application.

While the foregoing has illustrated and described what is now contemplated to be the best mode of carrying out the invention, the description is, of course, subject to modifications without departing from the spirit and scope of the invention. Therefore, it is not desired to restrict the invention to the particular construction illustrated and described, but to cover all modifications that may fall within the scope of the appended claims.

I claim:

1. In an applicator for contact lenses, comprising:
   (a) Means for ocularly applying contact lenses accommodated thereon;
   (b) Contact lens retaining means mountable on the contact lens applying means.

2. Applicator for contact lenses, according to claim 1, wherein closable housing means is provided for the contact lens applying and retaining means.

3. Applicator for contact lenses, according to claim 2, wherein the housing means is provided with external holding means for attachment to an object.

4. Applicator for contact lenses, according to claim 2, wherein the contact lens applying means extends perpendicularly and off-centered from the closure of the housing means.

5. Applicator for contact lenses, according to claim 1, wherein the contact lens applying means has at least one aperture, within which a contact lens may be accommodated.

6. Applicator for contact lenses, according to claim 5, wherein the contact lens retaining means has at least one aperture, which may be caused to coincide with that of the contact lens applying means when superposed thereon.

7. Applicator for contact lenses, according to claim 6, wherein the diameter of the apertures of the contact lens applying, respectively retaining means is substantially identical to or smaller than the diameter of the contact lens.

8. Applicator for contact lenses, according to claim 1, wherein the contact lens applying and retaining means, respectively constitutes a tray and an elongated member slidably mountable on the tray.

9. Applicator for contact lenses, according to claim 8, wherein edge portions of the elongated member are bent downwardly inward to form passages, within which edge portions of the tray may slide.

10. Applicator for contact lenses, according to claim 8, wherein a center portion of the elongated member is curved.

* * * * *